United States Patent
Marshall et al.

(10) Patent No.: US 6,656,163 B1
(45) Date of Patent: Dec. 2, 2003

(54) INJECTION DEVICES

(75) Inventors: Jeremy Marshall, Oxford (GB); Stuart Weekes, Oxford (GB)

(73) Assignee: Ares-Trading S.A., Vaumarcus (CH)

( * ) Notice: Subject to any disclaimer, the term of this patent is extended or adjusted under 35 U.S.C. 154(b) by 0 days.

(21) Appl. No.: 09/486,079

(22) PCT Filed: Aug. 20, 1998

(86) PCT No.: PCT/GB98/02495

§ 371 (c)(1),
(2), (4) Date: Feb. 22, 2000

(87) PCT Pub. No.: WO99/10030

PCT Pub. Date: Mar. 4, 1999

(30) Foreign Application Priority Data

Aug. 21, 1997 (GB) ............................................. 9717578
Aug. 29, 1997 (GB) ............................................. 9718221

(51) Int. Cl.⁷ ................................................. A61M 5/32
(52) U.S. Cl. ................... 604/198; 604/187; 604/197; 604/232; 604/111; 222/325; 222/326
(58) Field of Search ............................ 604/82, 411, 87, 604/88, 412, 414, 256, 905, 187, 192, 194–201, 205, 218, 232, 234, 235, 244, 263, 68, 243, 111, 110; 285/237, DIG. 2; 215/355, DIG. 8; 222/548, 326, 325, 386

(56) References Cited

U.S. PATENT DOCUMENTS

| | | | |
|---|---|---|---|
| 4,493,348 A | 1/1985 | Lemmons | |
| 4,507,113 A | 3/1985 | Dunlap | |
| 4,662,878 A | 5/1987 | Lindmayer | |
| 5,041,088 A | * 8/1991 | Ritson et al. | 604/135 |
| 5,042,977 A | * 8/1991 | Bechtold et al. | 604/134 |
| 5,171,214 A | 12/1992 | Kolber et al. | |
| 5,295,965 A | * 3/1994 | Wilmot | 604/136 |
| 5,478,316 A | * 12/1995 | Bitdinger et al. | 604/134 |
| 5,609,577 A | * 3/1997 | Haber et al. | 604/110 |
| 5,681,291 A | * 10/1997 | Galli | 604/156 |
| 6,241,709 B1 | * 6/2001 | Bechtold et al. | 604/207 |

FOREIGN PATENT DOCUMENTS

| | | | |
|---|---|---|---|
| FR | 1.257.066 | | 7/1961 |
| WO | WO 94/11041 | | 5/1994 |
| WO | WO 94/21316 | * | 9/1994 |
| WO | WO 96/32974 | | 10/1996 |

* cited by examiner

Primary Examiner—Brian L. Casler
Assistant Examiner—Cris Rodriguez
(74) Attorney, Agent, or Firm—Young & Thompson

(57) ABSTRACT

An injection device is disposable, and is designed to have a reusable firing mechanism fitted to its rear end. A syringe carrier within the barrel of the device is initially locked in a position with the needle of the syringe retracted by a locking element inserted laterally through the barrel. This element also holds an axially movable connector to which the firing mechanism connects. The device is made operable by removal of the locking element, and after use a return spring ensures that neither the syringe carrier nor the connector assume positions where the locking element can be reinserted. An adaptor may be provided to facilitate preparing a syringe with a two-component dose, and for disposal after use the adaptor with an empty vial still attached can be fitted to the rear end of the injection device in place of the firing mechanism.

17 Claims, 3 Drawing Sheets

Figure 7:
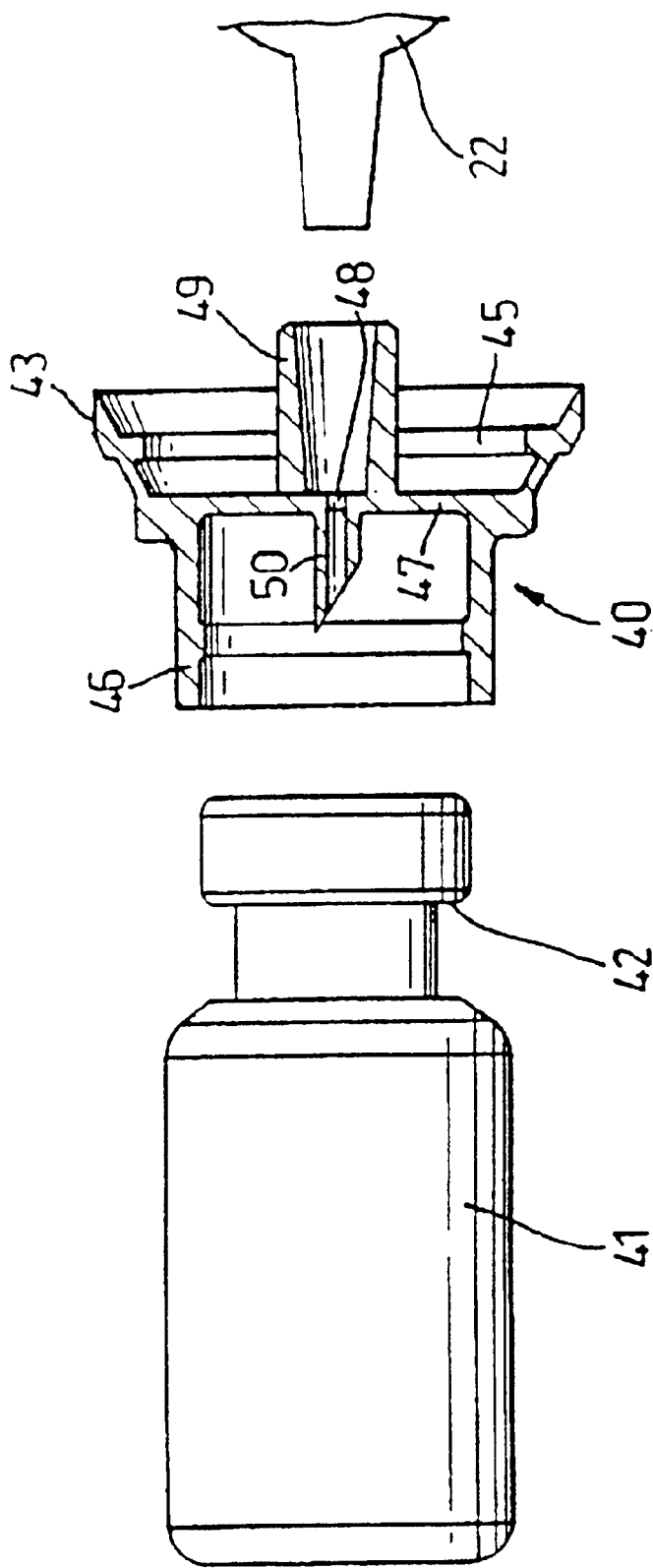

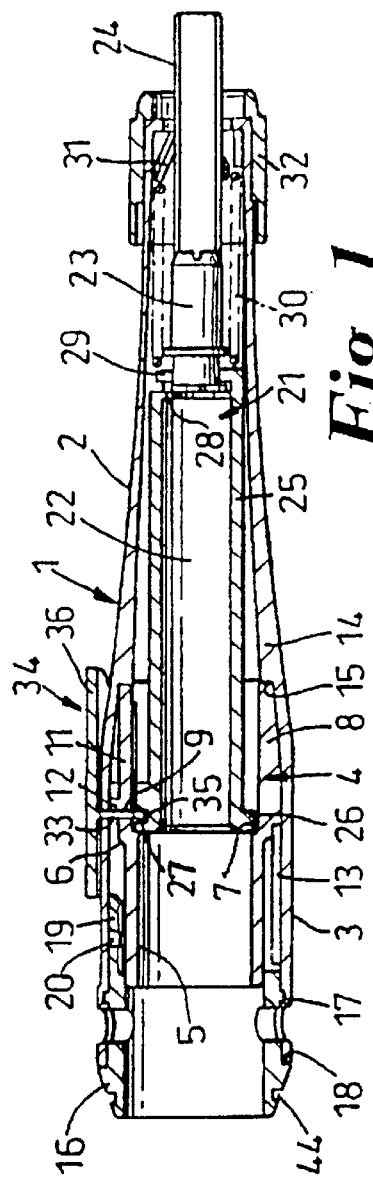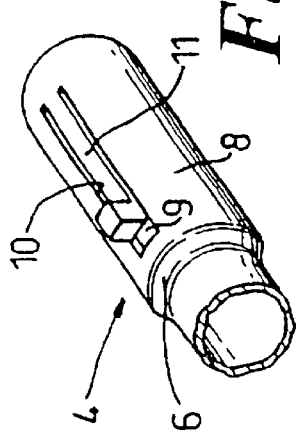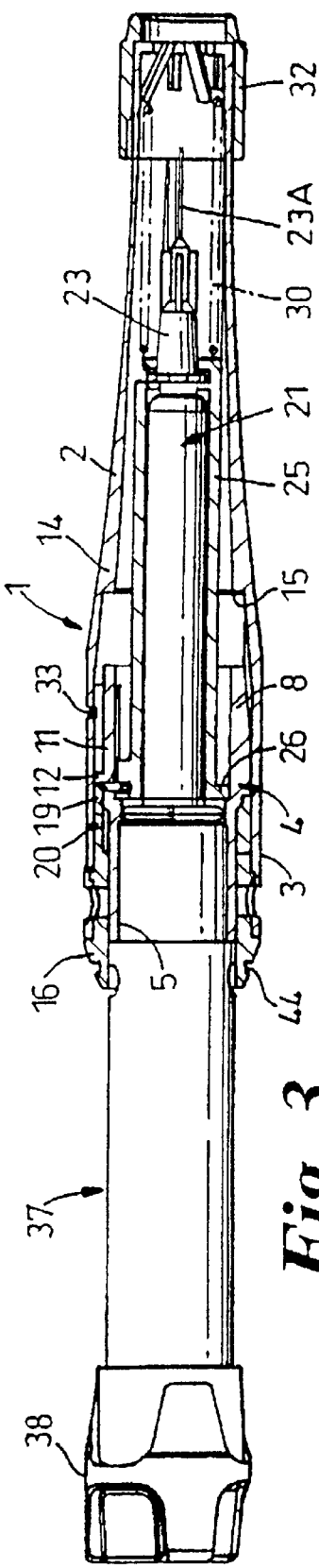
Fig. 1
Fig. 2
Fig. 3

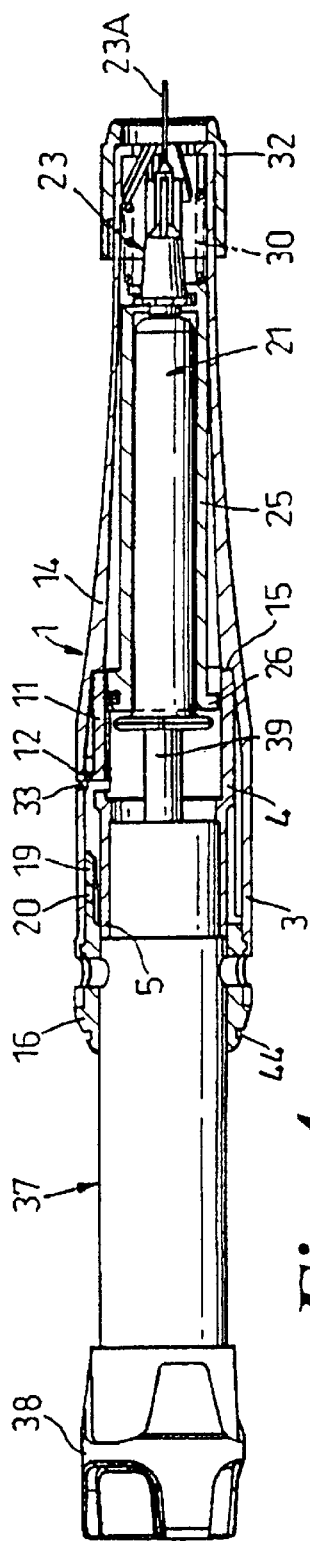
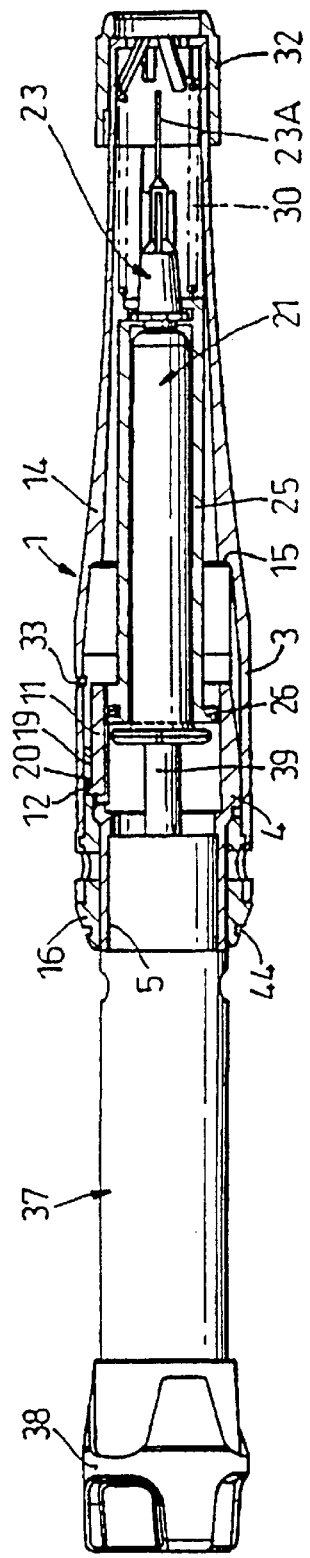
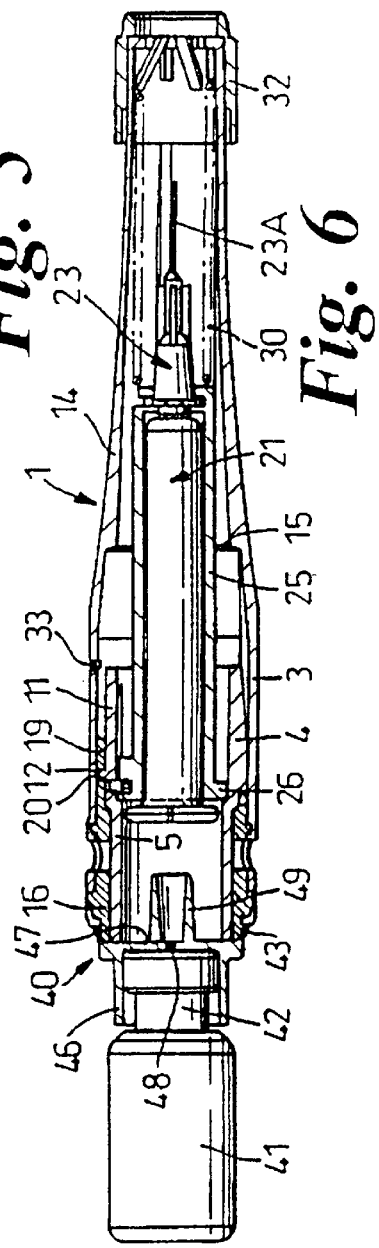
Fig. 4
Fig. 5
Fig. 6

INJECTION DEVICES

This invention relates to injection devices.

After any injection, the syringe with its needle is thrown away into a guarded enclosure, for obvious safety reasons. But removing it from a re-usable device that first fires the syringe forwards to make the needle penetrate, then pushes the syringe piston forwards to eject the dose, and which finally withdraws the syringe and needle, can itself be hazardous and time-consuming.

One answer is to discard everything, but such injection devices are complex and expensive. That is not therefore a realistic option.

However, by making the device in two parts, one being a re-usable firing mechanism with a plunger that can be released to spring forwards, and the other being a housing and guide for the syringe to which the firing mechanism can be temporarily attached, it becomes possible to contemplate throwing away this other part (still containing a syringe)

It is also useful to be able to tell at a glance whether a device has been used or not, and to have some safety measure that will positively prevent projection of the needle both before and after use.

It is the aim of this invention to provide such a device.

According to one aspect of the present invention there is provided an injection device comprising a barrel, a syringe carrier within the barrel axially movable between a rearward position, in which the needle of a syringe carried thereby is retracted within the forward end of the barrel, and a forward position, in which the needle projects from the forward end of the barrel, spring means urging the syringe carrier towards the rearward position, and a connector with limited freedom of axial movement at the rear end of the barrel for attachment of a firing device whose firing member, when released, acts on the piston in the syringe to urge the syringe forwards and then to eject a dose, wherein at least one of the connector and the syringe carrier is initially held rigid with the barrel by a removable locking element inserted laterally through the barrel, wherein on removal of the locking element, the connector and the syringe carrier assume positions, when the barrel is held against the skin by the firing device being pressed forwards, for the carrier and its syringe to be propelled forwards on actuation of the firing device, and wherein the syringe carrier reverts under the influence of the spring means to a rearward position after removal of the injection device from the skin.

Thus the device is manifestly in a non-usable condition as long as the locking element is in place. If it has been removed, it signifies that the device has been used and should be discarded. It is of course not just a visual signal; it is primarily a physical barrier to operation.

In order to ensure that the locking element cannot be replaced after use, and thus give the impression of a fresh injection device, it will preferably be arranged that either or both the connector and the syringe carrier finish at respective positions where their detents that were originally engaged by the locking element are no longer in registry with the aperture in the barrel through which the locking element was entered. The connector may have a snap engagement with a detent internal of the barrel to capture it in its after use position, while the spring means can urge the carrier to the rear of its locked position.

Preferably the spring means will be partially energised in the initial locked position, so that when the locking element is removed, the spring means will urge the syringe carrier rearwardly, bringing the tip of the needle further back into the barrel from a nearly projecting position which enables the cap to be removed. At the same time, the carrier may act on the connector to push that rearwardly, although not so far that it is captured in its ultimate after use position. Conveniently, a snap engagement element on the connector is rendered inoperative before firing of the device by interengagement of the syringe carrier and the connector, said element in that inoperative state forming a stop that limits rearward movement of the connector.

After injection, the spring means will act through the carrier, the syringe and the firing member to cause the reversion of the connector to its rearward, captive position, the axial relationship between the syringe carrier and the connector having changed and removed the interengagement that rendered the snap engagement element inoperative and limited the rearward movement before firing.

Conveniently, the attachment of the firing device to the connector is by mating screw threads, the connector being restrained against rotation with respect to the barrel.

The connector may be a stepped tube, the smaller diameter portion at the rear end providing a socket to receive the firing device, the internal forward facing shoulder formed by the step providing an abutment for the rear end of the syringe carrier, and the external, rearward facing shoulder formed by the step providing an abutment for engagement with a locking ring, fitted to the rear end of the barrel, when the connector is at its after use position.

The syringe carrier may have its limit of forward movement defined by an abutment internal of the barrel. This can be provided by the rear end of guide means for keeping the syringe carrier co-axial with the barrel, and against which a flange at the rear end of the syringe carrier will abut. The flange may also provide the detent in which the locking element engages.

The spring means is conveniently a helical spring surrounding a needle unit to engage the forward end of the syringe carrier and reacting against an abutment within the forward end of the barrel.

Preferably, the forward end of the barrel is equipped internally with barbs which point towards the mouth. They will allow projection of the needle and removal of the needle cap, but make it virtually impossible to poke a finger in and contact the retracted needle.

The roots of the barbs conveniently provide the abutment for the spring.

Such an injection device is primarily intended for use with a syringe containing a two component dose, these components having to be mixed immediately before injection. One component is a liquid (which may simply be water) already within the syringe, while the other component is a powder, to be dispersed in or made into a solution with the liquid.

A further aim of this invention is to ease the mixing process, and the disposal of the container of the second component along with the used syringe.

According to another aspect of the present invention there is provided an adaptor for use in preparation of a syringe dose, the syringe initially containing a liquid, being without its needle assembly, and having a piston to which a rod can be temporarily attached, the dose to be administered being a mixture of the liquid and a substance loosely contained in a sealed vial with a membrane over its neck, the adaptor comprising a cup member with a centrally apertured base, the cup being adapted to fit closely over the neck of the vial and having a central hollow spigot upstanding from the base that will pierce the membrane of the vial when the cap is fitted to the vial, and a formation on the outside of the base adapted to attach to the rear end of an injection device, which for use has a firing device fitted to that rear end, the formation having a recess communicating with the central aperture and shaped closely to receive the neck of a syringe, wherein the adaptor enables (when the vial and syringe are fitted to said cup and said recess respectively) injection of the liquid through the aperture and said spigot into the vial, to mix with said substance, and subsequently the withdrawal of the mixture back into the syringe, which is then transferable to the injection device to co-operate with its needle assembly, and wherein, after use of the injection device, the firing device is replaceable by the adaptor with the vial still attached.

Said formation may be a second cup, back-to-back and having a common base with the first cup, and a central spigot formed with said recess, the second cup fitting over the rear end of the injection device. Alternatively, the formation may include an externally screw threaded plug that screws into a connector socket to which the firing device can fit.

While the injection is performed the adaptor and empty vial combination is laid aside, but after the injection the combination is fitted to the injector device and, when that is disposed of, so is the adaptor and vial.

For a better understanding of the invention one embodiment will now be described, by way of example, with reference to the accompanying drawings, in which FIG. 1 is an axial section of an injection device as supplied, without any firing mechanism.

FIG. 2 is a detail, in perspective, of part of the device,

FIG. 3 is an axial section of the device with the firing mechanism fitted and ready for use, FIG. 4 is an axial section of the device with its firing mechanism during injection, FIG. 5 is an axial section of the device after injection, FIG. 6 is an axial section of the device with the firing mechanism removed and an adaptor fitted, ready for disposal, and FIG. 7 is an axial section of a vial adaptor, which forms an accessory to the device, and a vial.

The device has a barrel 1 with a tapered forward part 2 and a generally cylindrical rear part 3. Telescoped into this rear part 3 there is a stepped connector tube 4 whose reduced diameter rear end portion 5 forms a screw-threaded socket. At the mid-length there is an external, rearwardly facing shoulder 6 and an internal, forwardly facing shoulder 7. Just forward of these shoulders, the forward end portion 8 has an aperture 9 whose purpose is described later. Actually, as best seen in FIG. 2, this aperture 9 is the base of a narrow U-shaped slot 10 which forms a finger 11 effectively hinged to the portion 8 at its forward end by the resilient flexibility of the plastics material of which it is formed. At the rear end, the finger 11 has an outwardly projecting lug 12. The tube 4 is prevented from rotating with respect to the barrel 1 by a spline 13 on the interior of the barrel engaged in a groove in the portion 8.

The barrel is formed with internal guide ribs 14 over most of the tapered forward part 2, these terminating in rearwardly facing shoulders 15. The barrel is also extended rearwardly a short distance by a ring 16 which sleeves between the part 3 and the reduced diameter portion 5 of the tube 4, being retained by a snap fit rib and groove arrangement 17 and having a shoulder 18 abutting against the rear end of the barrel. The ring 16 has a forwardly projecting tongue 19 with an aperture 20 and a bevelled end.

Within the barrel 1 there is a syringe 21 comprising a capsule 22 with a needle unit 23 at its forward end, the actual needle 23A initially being encased by a cap 24. The capsule 22 is enclosed and carried by a sleeve 25 which has an outwardly projecting rim 26 at its rear end, locally thickened to accommodate a notch 27 which registers with the aperture 9 when the rear end of the sleeve 25 is up against the shoulder 7. At the forward end, the sleeve 25 has inturned flanges 28 and 29, the rear one 28 providing an abutment for the base of the needle unit 23 and the forward one 29 being U-shaped so that the base of the needle assembly can be entered laterally. That is done during manufacture, and the user never has access to the needle 23A except when it is actually performing the injection. The rear end of a helical spring 30 abuts the flange 29 and its forward end engages a guide formation 31 comprising several fingers, symmetrically arranged around the axis of the barrel to form barbs pointing inwards and forwards to terminate in the mouth of the barrel 1. These barbs can flex as necessary to allow the cap 24 to be extracted, and they do not impede the projection of the needle 23A. But they do provide an effective barrier to finger penetration. The mouth of the barrel is surrounded by a nose piece 32, which may be removed to increase the depth of penetration of the needle into the patient.

There is an aperture 33 in the cylindrical part 3 of the barrel which initially registers with the aperture 9. A T-shaped locking member 34 has a short stem 35 and a long asymmetrical cross member 36, and the stem 35 is inserted through the apertures 33 and 9 for its tip to engage in the notch 27 while the cross member 36 lies lengthways closely against the barrel, extending over the beginning of the tapered portion 2 and so affording a gap by which it can be prised away. In the assembled and "as supplied" condition of FIG. 1, this locking member 34 ensures that the syringe carrier 25 is positively held against any longitudinal movement. It also holds the connector tube 4 with its forward end abutting the shoulders 15.

This device is designed to be fitted to a known firing mechanism 37 which will not be described in detail. But it has a trigger button 38 at its rear end which, when operated, projects a plunger 39 from its forward end, and it screws into the socket 5. Preferably, the button 38 will have a safe position from which it has to be twisted before it can be pressed to release the plunger.

This mechanism 37 is fitted immediately before use, and then the cap 24, which projects beyond the barrel 1, is pulled away to expose the needle 23A within the barrel. Finally the locking member 34 is removed, having prevented the syringe and its carrier being dragged forwards when the cap 24 is being pulled off. The spring 30, which has been under slight compression, can now exert itself and push the barrel 1 forwardly until the forward end of the tongue 19 comes up against the lug 12. In this position the lug 12 cannot deflect under the tongue 19 due to the rim 26 of the sleeve 25. This is the position of FIG. 3.

The nose-piece 32 is then applied to the skin and the firing mechanism 37 pressed forwards, telescoping into the barrel until the tube 4 is arrested by coming up against the shoulders 15 again. This brings the tip of the needle 23A back into the mouth of the barrel, but not quite projecting. The button 38 is pressed to fire the plunger 39 forwards. This rapidly pushes the syringe assembly forwards to project the needle 23 and penetrate the skin. The spring 30 is of course compressed, being weaker than that of the firing device. When the syringe assembly reaches its forward limit, which may be defined by the rim 26 meeting the shoulders 15 or by the spring 30 being fully compressed, the plunger 39 carries on to urge the piston (not shown) within the capsule 22 forwards to eject the dose. This is the position of FIG. 4.

After that, the device is withdrawn, and the spring 30 exerts itself to push the barrel 1 forwards and thereby move the needle 23A further within the barrel until the lug 12 is engaged in the aperture 20. The lug 12 meets the bevelled end of the tongue 19, and as the rim 26 of the sleeve 25 is no longer under the lug 12, the finger 11 can flex inwardly before snapping back outwardly at the point where the shoulder 6 meets a step in the locking ring 16. The locking ring and barrel are therefore trapped and cannot shift rearwardly again. This is the position of FIG. 5.

Finally the firing mechanism 37 is removed, and replaced by a vial adaptor 40 which has been used prior to the injection. The assembly of FIG. 6 is then ready for disposal.

In this embodiment, the locking element 34 engages both the connector 4 and the syringe carrier 25 to hold them rigid with the barrel. This is preferred, since it makes insertion of the syringe 21 and attachment of the firing mechanism simple and certain. However, the device could be made inoperative by locking either the connector 4 or the syringe carrier 25, particularly the latter.

Referring to FIG. 7, the vial adaptor 40 is provided to simplify the process of preparing the syringe 21. Initially, the capsule 22 contains a liquid, while a vial 41 contains a substance, such as a lyophilised powder occupying only a fraction of the space within the vial. The dose to be administered is a mixture of the liquid and the substance, and so the latter has to be transferred to the syringe.

The vial 41 has a neck 42 across the end of which is a membrane which initially seals in the powder. The adaptor 40 is, in effect, two cups base-to-base, and one cup 43 is adapted to snap over the ring 16, which is provided with an annular groove 44 to receive a rib 45 on the inside of that cup. The other cup 46 is adapted to receive and retain, by a tight push fit or a snap-in action for example, the neck 42 of the vial 41. The common base 47 of the cups has a small central aperture 48 with a wide co-axial tubular spigot 49 on the side of the cup 43, and a narrow co-axial tubular spigot 50 on the side of the cup 46. This spigot has a sharp free end, for example by making it oblique to the axis, while the larger spigot 49 has an internal Luer taper to receive the needle-less forward end or neck of the syringe capsule 22. The piston within the capsule has a screw threaded socket on its rear facing side to receive a removable piston rod, which is fitted for the charging process as follows.

The neck 42 of the vial 41 is plugged into the cup 43 and then the neck of the capsule 22 is plugged into the spigot 49, this action causing the spigot 50 to pierce the membrane. The piston within the capsule 22 is then urged forwards by the temporary rod, forcing the liquid through the aperture 48 into the vial 41. It mixes with the substance, and this may be aided by shaking. When all the powder has dispersed, the piston is withdrawn, drawing the mixture back into the capsule 22. The piston rod is removed, and the capsule is unplugged and transferred to the sleeve 25.

The still attached combination of the adaptor 40 and vial 41 is set aside during the injection, but afterwards, when the firing mechanism 37 has been removed from the connector tube 4, the free cup 43 of the adaptor 40 is snap fitted over the rear end of the locking ring 16. Thus the injection device with the spent syringe, the adaptor 40 and the empty vial 41 can be discarded together as a unit.

Instead of the cup 43 fitting to the ring 16, use could be made of the screw threaded socket provided by the rear end portion 5 of the connector 4. The adaptor 40 would have a complementary male plug surrounding the spigot 49 (or that could be thickened and externally screw threaded) to screw into the connector 4.

What is claimed is:

1. An injection device comprising:

i) a barrel with an opening at a forward end, ii) a syringe carrier within the barrel and axially movable between a rearward position, in which a syringe carried thereby is retracted so that its needle is non-projecting from said forward end, and a forward position, in which the needle projects from said forward end, iii) spring means acting between the barrel and the syringe carrier to urge the syringe carrier rearwardly, iv) a connector with limited axial movement carried within the barrel and receiving the rear end of the syringe carrier within its forward end, v) a removable locking element inserted laterally through the barrel to engage and hold at least one of the connector and the syringe carrier against axial movement, its removal freeing both for axial movement, and vi) a locking element on the connector that snap fits to the barrel, the locking element being prevented from engaging the barrel before use and during injection, wherein forward movement of the carrier relative to the connector upon effecting an injection frees the locking element to snap fit to the barrel when, after injection, the spring means urges the carrier, and hence the syringe and the connector, rearwardly, vii) and wherein the rear end of the connector is adapted to receive a firing device, the firing device having an element to engage a piston within the syringe so that, when fired with the connector at its forward position, the syringe with its carrier is first thrust forwards to project the needle from the forward end of the barrel by the element acting through the piston and the dose within the syringe and then the piston is urged forwards to eject the dose.

2. An injection device as claimed in claim 1, characterised in that, after use, the connector (4) finishes at a position where a detent (9) therein that was originally engaged by the locking element (34) is no longer in registry with an aperture (33) in the barrel (1) through which the locking element (34) was entered.

3. An injection device as claimed in claim 2, characterised in that the connector (4) has a snap engagement with a detent (20) internal of the barrel (1) to capture it in its after use position.

4. An injection device as claimed in claim 3, characterised in that the spring means (30) is partially energised in the initial locked position, so that when the locking element (34) is removed, the spring means (30) urges the syringe carrier rearwardly, bringing the tip of the needle (23A) further back into the barrel (1) from a nearly projecting position which enables the cap (24) to be removed.

5. An injection device as claimed in claim 4, characterised in that the syringe carrier (25) is arranged to act on the connector (4) to push that rearwardly on removal of the locking element (34), although not so far that it is captured in its ultimate after use position.

6. An injection device as claimed in claim 5, characterised in that a snap engagement element (11, 12) on the connector (4) is rendered inoperative before firing of the device by interengagement of the syringe carrier (25) and the connector (4), said element (11, 12) in that inoperative state forming a stop that limits rearward movement of the connector (4).

7. An injection device as claimed in claim 6, characterised in that, after injection, the spring means (30) acts through the syringe carrier (25), the syringe (21) and a firing member

(39) of the firing device (37) to cause the reversion of the connector (4) to its rearward, captive position, the axial relationship between the syringe carrier (25) and the connector (4) having changed and removed the interengagement that rendered the snap engagement (11, 12) inoperative and limited the rearward movement before firing.

8. An injection device as claimed in claim 1, characterised in that the syringe carrier (25) finishes at a position where a detent (27) therein that was originally engaged by the locking element (34) is no longer in registry with an aperture (33) in the barrel (1) through which the locking element was entered.

9. An injection device as claimed in claim 8, characterised in that the spring means (30) urges the syringe carrier (25) to the rear of its locked position.

10. An injection device as claimed in claim 1, characterised in that the connector (4) is restrained against rotation with respect to the barrel (1).

11. An injection device as claimed in claim 1, characterised in that the connector (4) is a stepped tube, a smaller diameter portion (5) at the rear end providing a socket to receive the firing device (37), an internal forward facing shoulder (7) formed by the step providing an abutment for the rear end of the syringe carrier (25), and an external, rearward facing shoulder (6) formed by the step providing an abutment for engagement by a locking ring (16), fitted to the rear end (3) of the barrel (1), when the connector (4) is at its after use position.

12. An injection device as claimed in claim 1, characterised in that the syringe carrier (25) has its limit of forward movement defined by an abutment (15) internal of the barrel (1).

13. An injection device as claimed in claim 12, characterised in that the abutment (15) is provided by a rear end of guide means (14) for keeping the syringe carrier (25) co-axial with the barrel (1), and against which a flange (26) at the rear end of the syringe carrier (25) will abut.

14. An injection device as claimed in claim 13, characterised in that the flange (26) also provides the detent (27) in which the locking element (34) engages.

15. An injection device as claimed in claim 1, characterised in that the spring means is a helical spring (30) surrounding a needle unit (23) to engage the forward end of the syringe carrier (25) and reacting against an abutment within the forward end (2) of the barrel (1).

16. An injection device as claimed in claim 1, characterised in that the forward end (2) of the barrel (1) is equipped internally with barbs (31) which point towards the mouth, these barbs (31) allowing projection of the needle (23A) and removal of the needle cap (24), but preventing insertion of a finger.

17. An injection device as claimed in claim 16, characterised in that roots of the barbs (31) provide the abutment for the spring (30).

* * * * *